United States Patent
Kwak et al.

(10) Patent No.: US 9,081,074 B2
(45) Date of Patent: Jul. 14, 2015

(54) METHOD AND APPARATUS FOR ACCELERATED PHASE CONTRAST MAGNETIC RESONANCE ANGIOGRAPHY AND BLOOD FLOW IMAGING

(75) Inventors: Yongjun Kwak, Cambridge, MA (US); Reza Nezafat, Newton, MA (US)

(73) Assignee: Beth Israel Deaconess Medical Center, Inc. (BIDMC, Inc.), Boston, MA (US)

( * ) Notice: Subject to any disclaimer, the term of this patent is extended or adjusted under 35 U.S.C. 154(b) by 240 days.

(21) Appl. No.: 13/590,602

(22) Filed: Aug. 21, 2012

(65) Prior Publication Data

US 2014/0056496 A1    Feb. 27, 2014

(51) Int. Cl.
| | |
|---|---|
| G06K 9/00 | (2006.01) |
| G01R 33/561 | (2006.01) |
| G01R 33/563 | (2006.01) |
| A61B 5/055 | (2006.01) |
| A61B 5/026 | (2006.01) |
| G06K 9/62 | (2006.01) |

(52) U.S. Cl.
CPC .......... *G01R 33/5611* (2013.01); *A61B 5/0263* (2013.01); *A61B 5/055* (2013.01); *G01R 33/56316* (2013.01); *G06K 9/6249* (2013.01)

(58) Field of Classification Search
None
See application file for complete search history.

(56) References Cited

U.S. PATENT DOCUMENTS

| | | | | |
|---|---|---|---|---|
| 8,111,893 | B2 * | 2/2012 | Chen et al. | 382/131 |
| 8,437,564 | B2 * | 5/2013 | Harmanci et al. | 382/248 |
| 8,699,773 | B2 * | 4/2014 | Akcakaya et al. | 382/131 |
| 2009/0060362 | A1 * | 3/2009 | Harmanci et al. | 382/238 |
| 2009/0161933 | A1 * | 6/2009 | Chen | 382/131 |
| 2012/0081114 | A1 * | 4/2012 | Weller et al. | 324/309 |
| 2012/0099774 | A1 * | 4/2012 | Akcakaya et al. | 382/131 |
| 2014/0056496 | A1 * | 2/2014 | Kwak et al. | 382/131 |

FOREIGN PATENT DOCUMENTS

WO    2009/082419 A1    7/2009

OTHER PUBLICATIONS

Kim, Daniel, et al. "Accelerated phase-contrast cine MRI using k-t Sparse-Sense." Magnetic Resonance in Medicine, vol. 67, Issue 4 pp. 1054-1064, Apr. 2012. Article first published online: Nov. 14, 2011. DOI: 10.1002/mrm.23088.*
King, K.F. and W. Sun; "Compressed Sensing With Vascular Phase Contrast Acquisition;" Proceedings of 17th Annual Meeting of the International Society for Magnetic Resonance in Medicine (ISMRM)—Honolulu; vol. 17; 2009; p. 2817.

* cited by examiner

*Primary Examiner* — Tahmina Ansari
(74) *Attorney, Agent, or Firm* — Cha & Reiter, LLC

(57) ABSTRACT

An apparatus and method process magnetic resonance image (MRI) data and other data from a subject, including image data corresponding to at least one of angiographic data, four-dimensional blood flow, neurological blood flow, abdominal blood flow, and peripheral blood flow in the subject, and applies a compressed sensing (CS) reconstruction method utilizing a complex difference of the image data as a sparsifying transform for imaging of at least one of blood flow and magnetic resonance angiography to output a reconstructed image of the blood flow and magnetic resonance angiography, in the subject with increased processing speed and having high accuracy. The apparatus receives the MRI data of the fluid flow from an MRI device. The processor operates predetermined software, receives the MRI data, and applies the CS reconstruction method to generate the reconstructed image. An output device outputs the reconstructed image of the fluid flow.

31 Claims, 8 Drawing Sheets

METHOD AND APPARATUS FOR ACCELERATED PHASE CONTRAST MAGNETIC RESONANCE ANGIOGRAPHY AND BLOOD FLOW IMAGING

BACKGROUND OF THE INVENTION

1. Field of the Invention

The present invention relates to accelerated data acquisition for magnetic resonance imaging, and more particularly, to a compressed sensing reconstruction apparatus and method for imaging of the blood flow and angiography in the human body.

2. Description of the Related Art

Phase contrast (PC) cardiac magnetic resonance (CMR) imaging is widely used in the prior art for the clinical in-vivo assessment of blood flow in the diagnosing of various diseases and the depiction of the vessels in the body; for example, as described in Nayler et al., "Blood flow imaging by cine magnetic resonance", J Comput Assist Tomogr 1986; 10(5):715-722; Pelc et al., "Phase contrast cine magnetic resonance imaging", Magn Reson Q 1991; 7(4):229-254; and Rebergen et al., "Magnetic resonance measurement of velocity and flow: technique, validation, and cardiovascular applications", Am Heart J 1993; 126(6):1439-1456.

Through-plane aortic and pulmonic blood flow are measured and used for the evaluation of cardiac function and output, mitral regurgitation, and shunts. Clinically, a through-plane 2D image acquisition is performed for the evaluation of blood flow. Recent advances have also enabled 3D time-resolved PC image processing that allows quantification and visualization of the blood flow in all three directions, as described in Markl et al., "Time-resolved three-dimensional phase-contrast MRI", J Magn Reson Imaging 2003; 17(4):499-506. For quantitative measurement of cardiac indices such as cardiac output or mitral regurgitation, flow measurements should be accurate and reproducible. However, despite the potential of PC CMR as an alternative to Doppler ultrasound for evaluation of these indices, its accuracy is impacted by several limitations including background offset, eddy currents, and long scan time.

One of the challenges of PC CMR is the long scan time which limits spatial and temporal resolution. Several acquisition methods have been used to improve the data acquisition efficiency and reduce the total scan time in PC CMR; that is, increase the acceleration rate of image acquisition and reconstruction. Echo planar imaging has been used to improve the temporal resolution of flow imaging, such as in Ordidge et al., "Real time movie images by NMR", British Journal of Radiology 1982; 55(658): 729-733. Non-Cartesian k-space trajectories including spiral and radial sequences have also been used to reduce scan time, as described in Nayak et al., "Real-time color flow MRI", Magn Reson Med 2000; 43(2):251-258; Park et al., "Rapid measurement of time-averaged blood flow using ungated spiral phase-contrast", Magn Reson Med 2003; 49(2):322-328; and Barger et al., "Phase-contrast with interleaved undersampled projections", Magn Reson Med 2000; 43(4):503-509.

Parallel imaging methods are also used in the prior art, for example, in "Pruessmann et al., "SENSE: sensitivity encoding for fast MRI", Magn Reson Med 1999; 42(5):952-962; and Griswold et al., "Generalized autocalibrating partially parallel acquisitions (GRAPPA)", Magn Reson Med 2002; 47(6):1202-1210. Such parallel imaging methods, which have been widely used clinically for accelerated imaging, were shown to provide accurate flow measurements with reduced scan time, as described in Thunberg et al., "Accuracy and reproducibility in phase contrast imaging using SENSE", Magn Reson Med 2003; 50(5):1061-1068. The study by Baltes et al., "Accelerating cine phase-contrast flow measurements using k-t BLAST and k-t SENSE. Magn Reson Med 2005; 54(6):1430-1438; showed that k-t BLAST and k-t SENSE are promising approaches for high-resolution breath-hold flow quantification through the ascending aorta with up to 5-fold acceleration.

To overcome the limitation of the acceleration rate of the previous schemes, recent studies have shown that higher acceleration rate can be achieved using compressed-sensing (CS) when compared with more established techniques such as parallel imaging, as described in Tao et al., "Compressed sensing reconstruction with retrospectively gated sampling patterns for velocity measurement of carotid blood flow", Proceedings of the 18th Annual Meeting of ISMRM. Volume 18. Stockholm, Sweden; 2010. p 4866; Hsiao et al., "Quantitative assessment of blood flow with 4D phase-contrast MRI and autocalibrating parallel imaging compressed sensing", Proceedings of the 19th Annual Meeting of ISMRM. Volume 19. Montreal, Canada; 2011. p 1190; and Kim et al., "Accelerated phase-contrast cine MRI using k-t SPARSE-SENSE", Magn Reson Med 2012; 67(4):1054-1064.

Compressed sensing reconstruction with accelerated PC acquisitions is a promising technique to increase the scan efficiency. In a study by Tao et al., "Compressed sensing reconstruction with retrospectively gated sampling patterns for velocity measurement of carotid blood flow", Proceedings of the 18th Annual Meeting of ISMRM. Volume 18. Stockholm, Sweden; 2010. p 4866"; CS reconstruction is simulated with retrospectively gated 2D PC cine scans of carotid blood flow. The study by Hsiao et al., "Quantitative assessment of blood flow with 4D phase-contrast MRI and autocalibrating parallel imaging compressed sensing", Proceedings of the 19th Annual Meeting of ISMRM. Volume 19. Montreal, Canada; 2011. p 1190"; assessed the accuracy of flow quantification for 4D phase contrast MRI by comparing parallel imaging and CS.

Kim et al., "Accelerated phase-contrast cine MRI using k-t SPARSE-SENSE", Magn Reson Med 2012; 67(4):1054-1064; performed a combination of spatio-temporal (k-t)-based CS and parallel imaging, called k-t SPARSE-SENSE for prospectively under-sampled in-vivo data, and reported agreements between k-t SPARSE-SENSE and GRAPPA. While k-t approaches could surpass the acceleration that can be achieved using acceleration only in the spatial domain, k-t approaches could also cause temporal blurring. Stadlbauer et al., "Accelerated time-resolved three-dimensional MR velocity mapping of blood flow patterns in the aorta using SENSE and k-t BLAST", Eur J Radiol 2010; 75(1): e15-21; demonstrated that 6-fold k-t BLAST shows a reduction in peak velocity compared to rate 2 SENSE, which is caused by temporal blurring.

In a previous study in the prior art involving CS for PC utilizing the complex difference (CD) of two flow-encoded images, described in King et al., "Compressed sensing with vascular phase contrast acquisition", Proceedings of the 17th Annual Meeting of ISMRM. Volume 17. Honolulu, USA; 2009. p 2817; such an application of CS involved MR angiography with maximum intensity projection images in the brain, and was not applied to or involving flow assessment of blood or substances in living tissue, such as blood through a heart. However, the method of King does not use sparsifying in the complex difference domain, and the method only related to use of CS in addition to parallel imaging for angiography.

In addition, the aim of the method of King is to obtain MR angiography with no utilization of individual flow encoded images $m_1$, $m_2$, $m_3$, and $m_4$. The method of King uses CD images by combining all of such CD images to obtain one flow weighted image, which does not allow for extraction of flow measurements. As described in King, "Complex difference processing was used to calculate the flow images for each axis, e.g. for the x-axis, $$m_x = \sqrt{|m_1|^2 + |m_2|^2 - 2|m_1||m_2|\cos[\angle(m_1 m^*_2)]}$$

etc. where $M_{echo}$ refers to the image for each flow moment combination (echo=1, 2, 3, 4). The final flow image is given by:

$$m_{flow} = \sqrt{m_x + m_y + m_z}.$$

Furthermore, the method of King solves equations to process image data, but King states that "we added a sparsifying transform of the final flow image, giving the objective function which is:

$$J = \Sigma_{echo} [\|Em_{echo} - S_{echo}\|_2^2 + \lambda \|\Psi m_{echo}\|_1] + \lambda_{flow} \|\Psi m_{flow}\|_1"$$

where "m flow" is an image obtained by squareroot of sum of squares, which does not permit generating flow images or Calculate squareroot of sum of squares and create a MR angiogram.

Therefore, due to the deficiencies in the prior art in image acquisition and reconstruction methods for accurate and reproducible flow measurements at very high acceleration rates, alternative methods are needed that can enable acceleration of image acquisition and processing of blood flow in the human body without temporal blurring.

SUMMARY OF THE INVENTION

An apparatus includes a processor, operating predetermined software, for receiving the image data from a data source, wherein the image data corresponds to at least one of angiographic data, four-dimensional blood flow, neurological blood flow, abdominal blood flow, and peripheral blood flow in a subject, and for applying a compressed sensing (CS) reconstruction method utilizing a complex difference of the image data as a sparsifying transform for imaging of at least one of blood flow and magnetic resonance angiography to generate a reconstructed image of the at least one of blood flow and magnetic resonance angiography from the image data. The apparatus may also include an output device for outputting the reconstructed image, and a magnetic resonance image (MRI) system for obtaining the image data of the subject.

In addition, the apparatus and method of the present invention process magnetic resonance image (MRI) data to generate and output a reconstructed image of bodily fluid flow, such as blood flow, in the living subject with increased image processing speed and having high accuracy in the reconstructed images. The apparatus includes an input device, a processor, and an output device. The input device receives the MRI data of the fluid flow in the living subject from an MRI device having a plurality of coils, and generates selected image data from received inputs. The processor operates predetermined software, receives the selected image data, and applies a compressed sensing (CS) reconstruction method to the image data to generate reconstructed images from the image data. The output device outputs the reconstructed image of the fluid flow in the living subject.

BRIEF DESCRIPTION OF THE DRAWINGS

The above features and advantages of the invention will become more apparent from the following description taken in conjunction with the accompanying drawings in which.

DETAILED DESCRIPTION OF THE INVENTION

Hereinafter, preferred embodiments of the present invention will be described with reference to the accompanying drawings. In the following description, a detailed explanation of known related functions and constructions may be omitted to avoid unnecessarily obscuring the subject matter of the present invention. This invention may, however, be embodied in many different forms and should not be construed as limited to the exemplary embodiments set forth herein. The same reference numbers are used throughout the drawings to refer to the same or like parts. Also, terms described herein, which are defined considering the functions of the present invention, may be implemented differently depending on user and operator's intention and practice. Therefore, the terms should be understood on the basis of the disclosure throughout the specification. The principles and features of this invention may be employed in varied and numerous embodiments without departing from the scope of the invention.

Furthermore, although the drawings represent exemplary embodiments of the invention, the drawings are not necessarily to scale and certain features may be exaggerated or omitted in order to more clearly illustrate and explain the present invention.

As described herein, the term "phase contrast" is abbreviated "PC", and so the abbreviation "PC" refers to "phase contrast" throughout the present application. In addition, as described herein, the term "Total Variation", in reference to known methods such as "Total Variation regulation", is abbreviated "TV", and so the abbreviation "TV" refers to "Total Variation" throughout the present application.

Figure 1:
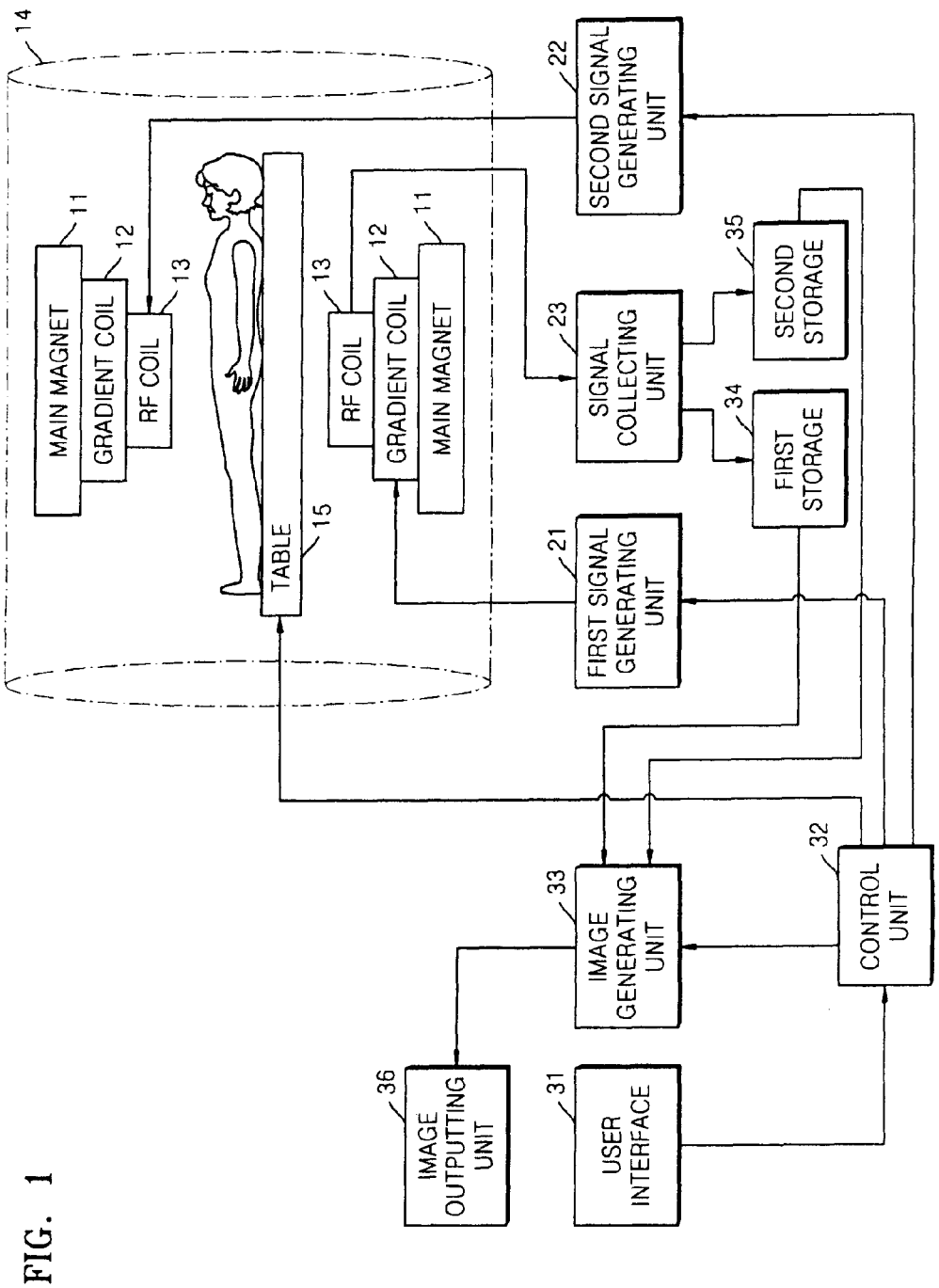
FIG. 1 is a diagram of a structure of a magnetic resonance imaging (MRI) apparatus according to an exemplary embodiment of the present invention.

FIG. 1 is a view illustrating a structure of a magnetic resonance imaging (MRI) apparatus or system according to an exemplary embodiment of the present invention, which obtains image data for imaging corresponding to any known blood flow and MR angiography. The image data may be angiographic data, four-dimensional blood flow data, neurological blood flow data, abdominal blood flow data, peripheral blood flow data, or data corresponding to any known fluid flow in a subject. Using the image data from the MRI apparatus in FIG. 1, the present invention applies a compressed sensing (CS) reconstruction method utilizing a complex difference of the image data as a sparsifying transform for imaging of blood flow or magnetic resonance angiography, as described in greater detail herein.

Referring to FIG. 1, the MRI apparatus may include a main magnet 11, a gradient coil 12, a radio frequency (RF) coil 13, a shield 14, a table 15, a first signal generating unit 21, a second signal generating unit 22, a signal collecting unit 23, a user interface 31, a control unit 32, an image generating unit 33, a first storage 34, a second storage 35, and an image outputting unit 36. The main magnet 11, the gradient coil 12, and the RF coil 13 are elements for generating a magnetic field to induce magnetic resonance signals from atomic nuclei inside a human body, and may be implemented as a magnet, coils, etc. The shield 14 blocks an electromagnetic wave generated by the RF coil 13 from being radiated to the outside. A target object, for example, a patient, lies on the table 15 inside the shield 14, and the table 15 may move by control of the control unit 32 to move in or out of the assembly of components 11-14, to position the patient for MRI photography.

The first signal generating unit 21, the second signal generating unit 22, and the signal collecting unit 23 are components for transmitting signals to generate the magnetic field in the gradient coil 12 and the RF coil 13 by the control of the control unit 32 or for collecting signals received in the RF coil 13 and providing the image generating unit 13 with the collected signals, and may be implemented as an oscillator, an amplifier, a modulator, a demodulator, an analog-to-digital converter (ADC), a digital-to-analog converter (DAC), etc. The user interface 31, the control unit 32, the image generating unit 33, the first storage 34, the second storage 35, and the image outputting unit 36 are components for controlling the first signal generating unit 21 and the second signal generating unit 22 or for processing signals collected by the signal collecting unit 23, and may be implemented as a computer and peripheral devices of the computer.

The main magnet 11 generates a static magnetic field for arranging directions of magnetic dipole moments of atomic nuclei, typically hydrogen nuclei in water molecules, inside the human body in one direction. Examples of the main magnet 11 for generating the static magnetic field include a permanent magnet, a room temperature electromagnet, a superconductivity electromagnet, etc. A magnetic field generated by the superconductivity electromagnet is strong and uniform, and thus the superconductivity electromagnet is mainly used as the main magnet 11. For example, if hydrogen atomic nuclei inside the human body are placed in the static magnetic field generated by the main magnet 11, directions of magnetic dipole moments of the hydrogen atomic nuclei are arranged in a direction of the static magnetic field generated by the main magnet 11 in order to go into a lower energy state. To maintain a thermal parallel state, the number of atomic nuclei in a low energy state is actually slightly greater than the number of atomic nuclei in a high energy state. In this regard, an energy difference between atomic nuclei in different energy states is proportional to an intensity of the static magnetic field generated by the main magnet 11, and has an intrinsic Larmor frequency associated with Larmor precession of the atomic nuclei. For example, if the intensity of the static magnetic field generated by the main magnet 11 is 1 Tesla, the Larmor frequency of a hydrogen atomic nucleus in the static magnetic field generated by the main magnet 11 is 42.58 MHz, and the Larmor frequency of a sodium atomic nucleus therein is 11.27 MHz.

The gradient coil 12 generates a gradient magnetic field that varies at a constant gradient with respect to each of a plurality of directions, for example, directions x, y, and z, in proportion to a distance from a reference location within the static magnetic field generated by the main magnet 11. In this regard, the reference location may be an origin point of a 3D coordinate system when a space including a static magnetic field generated by the main magnet 11 is presented as the 3D coordinate system. Each of the magnetic resonance signals received by the RF coil 13 has location information in a 3D space due to the gradient magnetic field generated by the gradient coil 12. The gradient coil 12 may comprise an X gradient coil for generating the gradient magnetic field that varies in the direction x, a Y gradient coil for generating the gradient magnetic field that varies in the direction y, and a Z gradient coil for generating the gradient magnetic field that varies in the direction z.

The RF coil 13 generates an electromagnetic wave signal having an RF corresponding to a type of an atomic nucleus, i.e., an RF signal, and applies the electromagnetic wave signal to the target object in order to transit the atomic nucleus from the low energy state to the high energy state. Atomic nuclei inside the target object are excited by the applied electromagnetic wave signal. In this regard, the target object is generally an MR image captured site of the human body, or may be a living body other than the human body or an inanimate object. For example, the RF coil 13 may generate the electromagnetic wave of 42.58 MHz to transit an energy state of the hydrogen atomic nucleus within the static magnetic field of 1 Tesla. Also, the RF coil 13 may generate the electromagnetic wave of 11.27 MHz to transit an energy state of the sodium atomic nucleus within the static magnetic field of 1 Tesla. If the electromagnetic wave signal generated by the RF coil 13 is applied to an atomic nucleus, the atomic nucleus is transited from a low energy state to a high energy state. Thereafter, if the electromagnetic wave signal generated by the RF coil 13 disappears, i.e. if the electromagnetic wave applied to the atomic nucleus disappears, the atomic nucleus radiates an electromagnetic wave having the same Larmor frequency while being transited from the high energy state to the low energy state.

The RF coil 13 receives an electromagnetic wave signal radiated from atomic nuclei inside the target object. The electromagnetic wave signal is referred to as a free induction decay (FID) signal. The FID signal is referred to as an echo signal with respect to the electromagnetic wave signal applied to the target object as a magnetic resonance signal used to generate a magnetic resonance image. A length of a time interval from a time point when the electromagnetic wave signal is applied to the target object, i.e. a time point when the electromagnetic wave signal is generated, to a time point when the electromagnetic wave signal is received from the target object is referred to as an echo time (TE). A length of a time interval when an application of the electromagnetic wave signal to the human body repeats is referred to as a repetition time (TR).

The RF coil 13 may be implemented as one coil having a function of generating an electromagnetic wave having an RF corresponding to a type of an atomic nucleus and a function of receiving an electromagnetic wave radiated from the atomic nucleus, or may be implemented as a transmission coil having the function of generating the electromagnetic wave having the RF corresponding to the type of the atomic nucleus and a reception coil having the function of receiving the electromagnetic wave radiated from the atomic nucleus. In particular, according to the present embodiment of FIG. 1, the reception coil of the RF coil 13 may be implemented as a dual tuned coil capable of receiving several frequencies in one coil, may be implemented as a multi-channel coil capable of simultaneously receiving a plurality of magnetic resonance signals, or may be implemented as a dual tuned multi-channel coil.

The user interface 31 receives a command from an operator of the MRI apparatus of FIG. 1 and outputs the command to the control unit 32. The user interface 31 may be implemented as a general input device of a computer, such as a keyboard and a mouse. The image outputting unit 36 outputs the magnetic resonance image generated by the image generating unit 33. The image outputting unit 36 may be implemented as a general output device of the computer such as a monitor. The control unit 32 controls the first signal generating unit 21, the second signal generating unit 22, the signal collecting unit 23, and the image generating unit 33 according to the command output from the user interface 31. The image generating unit 33 generates a magnetic resonance image by using magnetic resonance signals that are collected by the signal collecting unit 23 and are stored in the first storage 34 and the second storage 35. The control unit 32 and the image generating unit 33 may be implemented as a high performance computer capable of promptly processing a large amount of data required to generate the magnetic resonance image. Meanwhile, it will be understood by one of ordinary skill in the art that the terms "generating the magnetic resonance image" may be replaced by various terms such as reconstructing the magnetic resonance image.

The control unit 32 generates a control signal indicating an alternating signal having a frequency varying at a certain gradient with respect to each of the directions x, y, and z, and outputs the control signal to the second signal generating unit 22. The first signal generating unit 21 generates the alternating signal having a frequency varying at a constant gradient with respect to each of the directions x, y, and z according to the control signal received from the control unit 32, and outputs the alternating signal to the gradient coil 12. The gradient coil 12 generates a gradient magnetic field that varies at a constant gradient with respect to each of the directions x, y, and z according to the alternating signal received from the first signal generating unit 21. The control unit 32 generates a control signal indicating a pulse train, and outputs the control signal to the second signal generating unit 22. The second signal generating unit 22 generates an alternating signal having the pulse train according to the control signal received from the control unit 32, and outputs the alternating signal to the RF coil 13. The RF coil 13 generates an electromagnetic wave signal having the pulse train according to the alternating signal received from the second signal generating unit 22. The first signal generating unit 21 and the second signal generating unit 22 may be implemented as ADCs for converting analog signals received from the control unit 32 into digital signals, oscillators for generating source signals, modulators for modulating the source signals according to signals received from the control unit 32, amplifiers for amplifying the signals modulated by the modulators, etc. Such amplified signals are sent to the coils 12, 13.

The signal collecting unit 23 collects magnetic resonance signals induced by atomic nuclei through the RF coil 13. The signal collecting unit 23 may be implemented as an amplifier for amplifying magnetic resonance signals received from the RF coil 13, a demodulator for demodulating the magnetic resonance signals amplified by the amplifier, a DAC for converting analog magnetic resonance signals demodulated by the demodulator into digital magnetic resonance signals, etc. The magnetic resonance signals converted into digital form are separately stored in the first storage 34 and the second storage 35. The first storage 34 and the second storage 35 are not necessarily physically separated storages but are spaces for separately storing different types of magnetic resonance signals. For example, the first storage 34 and the second storage 35 may be different storage regions of a hard disk.

The RF coil 13 generates an electromagnetic wave from an alternating current applied from the second signal generating unit 22 to the RF coil 13, and receives an electromagnetic wave by a collection of signals by the signal collecting unit 23, and thus it is possible to freely adjust a time when the RF coil 13 generates a pulse and a time when the RF coil 13 receives the pulse.

In a preferred embodiment shown in FIG. 1, the image generating unit 33 performs the method for accelerated phase contrast magnetic resonance angiography and blood flow imaging as described herein with reference to FIGS. 3-8F.

Figure 2:
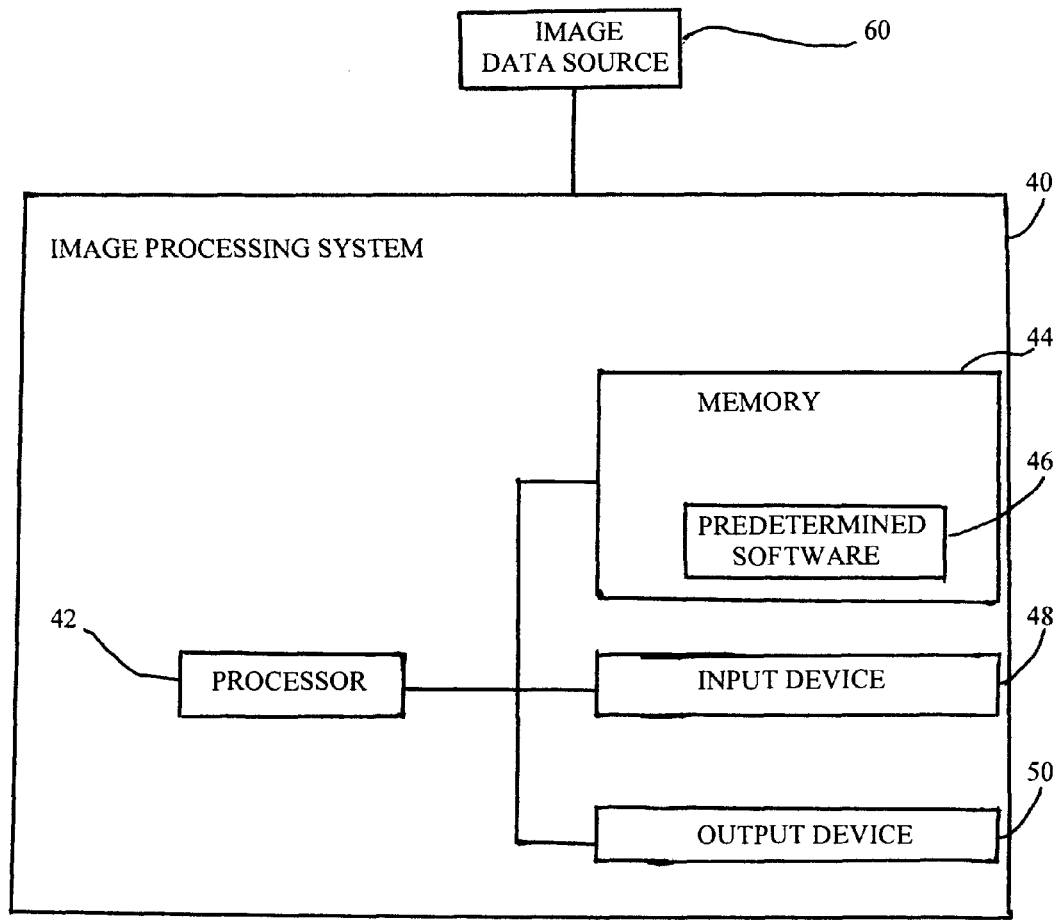
FIG. 2 is a block diagram illustrating an image processing system in accordance with an alternative exemplary embodiment of the present invention.

Referring to FIG. 2, in an alternative exemplary embodiment of the present invention, the apparatus performs the method for accelerated phase contrast magnetic resonance angiography and blood flow imaging as described herein with reference to FIGS. 3-8F, and includes an image processing system 40 having a processor 42, a memory 44 for storing data and operational programs such as predetermined software 46, an input device 48, and an output device 50. The output device 50 may include the image outputting unit 36 of FIG. 1, which may be a display, a printer, etc. for displaying reconstructed MRI images, or the output device 50 may be a communications interface for connecting to the image outputting unit 36. The input device 48 may include a keyboard and/or a mouse for receiving user inputs and selections, and may incorporate or be connected to the user interface 31 of FIG. 1. In addition, the input device 48 and the output device 50 may operate together to provide a graphic user interface (GUI), for example, provided to the user of the MRI apparatus by the user interface 31 in a manner known in the art. In alternative embodiments, the input device 48 and the output device 50 may include a touch screen to provide a GUI which responds to user touches, in a manner known in the art, for operating the image processing system 40 of the present invention.

In the alternative exemplary embodiment of FIG. 2, the image processing system 40 is a stand-alone computer, and the image reconstruction may be performed off-line; that is, independent of the image acquisition process of, for example, the MRI system of FIG. 1. Alternatively, the image reconstruction may be performed contemporaneously with the acquisition of images of a subject by the MRI system of FIG. 1.

The image reconstruction is performed using customized software, as the predetermined software 46 implementing the method 70 described herein, and generated using mathematical software development and authoring tools, such as "MATLAB", commercially available from "The MathWorks, Inc.", of Natick, Mass., USA.

The image processing system 40 receives and processes image data from an image data source 60, with the received image data stored in the memory 44. The image data source 60 may include the entire MRI apparatus of FIG. 1, which may be implemented using, for example, a "1.5 T ACHIEVA" magnet as the main magnet 11, commercially available from Philips Healthcare, of Best, The Netherlands, which has a 5-channel coil for performing cardiac MRI measurements on the cardiac region of a subject, such as a patient. In the alternative exemplary embodiment of FIG. 2, the image data source 60 is operatively connected by a wired and/or wireless connection to the image processing system 40. The image data source 60 may also be embodied as one or both of the first storage 34 and the second storage 35 in FIG. 1 for receiving and storing data corresponding to RF signals, MR signals, and other known data signals from the respective coils 12, 13.

In further alternative embodiments, the image processing system 40 is connected, using a wired and/or wireless connection, to a computer network, such as the Internet, and receives the image data from at least one or even multiple remote sources, such as medical image data archives as the image data source 60. For example, the MRI images collected by a hospital or other MRI facilities, for example, using the apparatus of FIG. 1 or other known MRI apparatus, may store the images in a storage facility as the image data source 60, which may be remotely accessed by the image processing system 40 of the present invention using known communication devices and methods.

Figure 3:
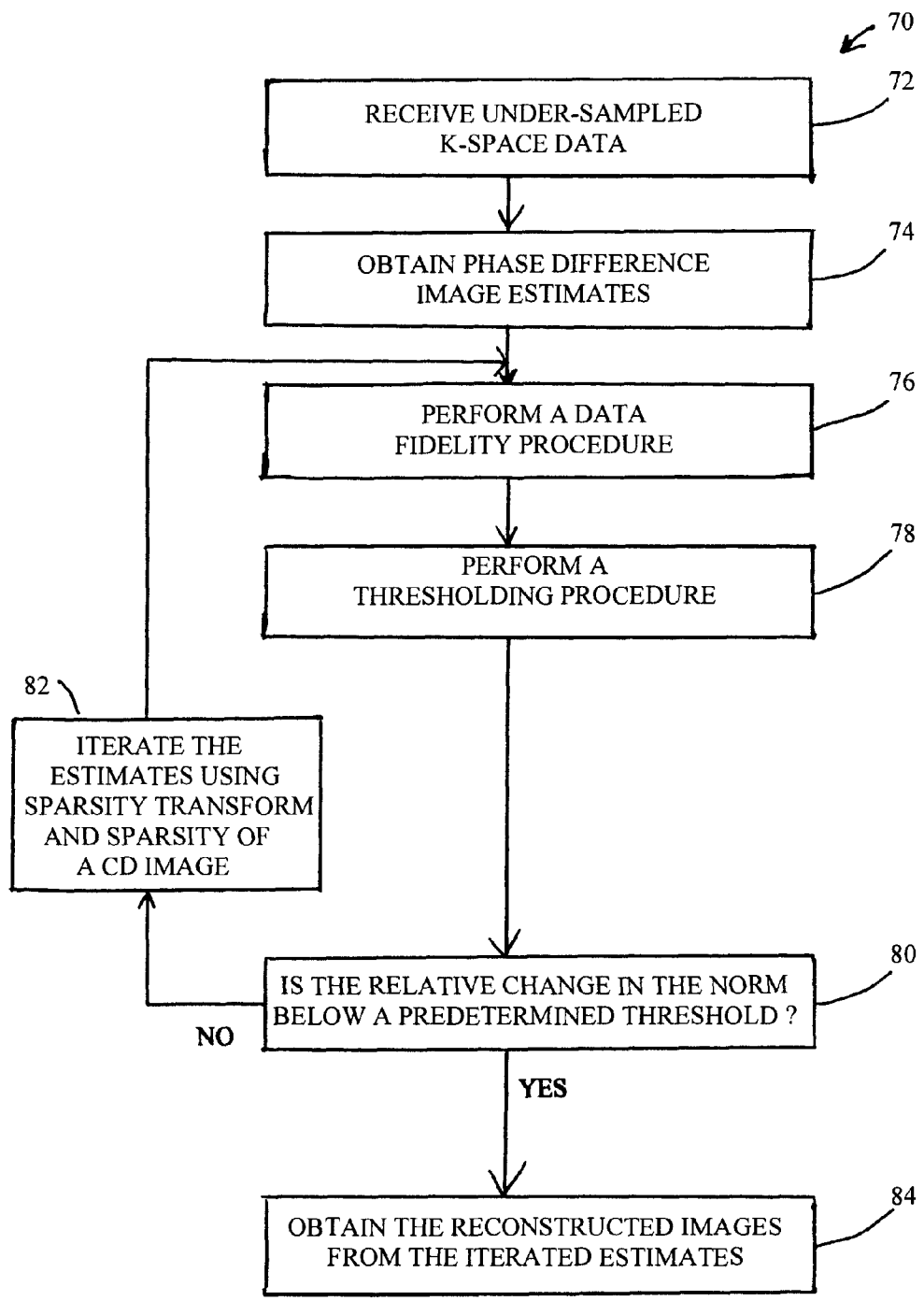
FIG. 3 is a flowchart illustrating a method in accordance with the exemplary embodiment of the present invention.

Referring to FIG. 3, the predetermined software 46 implements a method 70 for performing image reconstruction from the image data received from the image data source 60. The method includes the steps of receiving under-sampled K-space data in step 72, for example, under-sampled by an acceleration rate of five, obtained from the full K-space MRI data from the MRI device, obtaining phase difference image estimates in step 74, performing a data fidelity procedure in step 76, performing a thresholding procedure in step 78 using a sparsifying transform and a sparsity of the complex difference (CD) image, and checking whether a relative change in the norm of the image estimates between iterations is below a predetermined threshold in step 80. If not, the method 70 iterates the image estimates in step 82 using the sparsity transform and the sparsity of the CD image, and loops back to step 76. The iteration in steps 76-82 is repeated until the condition of step 80 is met, and then the method obtains the reconstructed images from the final iterated image estimates in step 84. The reconstructed images may then be stored, transmitted, and/or output by the image processing system 40, for example, using the output device 50.

As described in greater detail herein, the present invention utilizes the sparsity of the complex difference (CD) of the two flow-encoded images as an additional constraint term to improve the CS reconstruction of the corresponding accelerated PC image data acquisition. Using retrospectively under-sampled data from step 72, the apparatus 40 and method 70 of the present invention implement a reconstruction technique for generating reconstructed images from the received image data. In experimental use, the apparatus 40 and method 70 of the present invention were optimized and validated in-vivo on fifteen healthy subjects. Then, prospectively under-sampled data was acquired in step 72 from eleven healthy subjects, and images of the subjects were reconstructed with the apparatus 40 and method 70 of the present invention. The results show that there is good agreement between the cardiac output measurements from the fully-sampled data and the proposed CS reconstruction method using CD sparsity up to acceleration rate of five; that is, having an increased image processing speed five times the normal unaccelerated speed. In addition, the CS reconstruction method in the prior art without CD image processing shows 300% more under-estimated flow results compared to the flow results of the present invention.

In the apparatus 40 and method 70 of the present invention, an inventive accelerated PC MRI approach is implemented, as described herein, in which the sparsity of the complex difference image for each individual phase is used as an additional sparsifying transform in step 78 in compressed-sensing reconstruction for the quantitative evaluation of blood flow in the subjects. Initially, the accuracy of the proposed reconstruction method is evaluated by retrospectively discarding data from a fully-sampled k-space to generate the under-sampled k-space data in step 72. Subsequently, an accelerated data acquisition is performed in a cohort of healthy subjects to evaluate the accuracy and reproducibility of the disclosed accelerated data acquisition and reconstruction method 70.

PC images are typically reconstructed using the phase difference between two image data sets with different bipolar encoding gradients. Assuming the bipolar gradient is applied for the slice selection gradient, the complex MR signal $s_1(k_x, k_y)$ from a moving magnetization $m_1(x, y)$ with a velocity vector $v_z(x,y)$ in the z-direction for each point in the x-y plane can be expressed as:

$$s_1(k_x,k_y) = \iint_{x,y} m_1(x,y) e^{-i[2\pi(k_x x + k_y y) - \gamma M_z v_z(x,y)]} dx dy \quad (1)$$

where $M_z$ is the first moment of the bipolar gradient and $\gamma$ is the gyromagnetic ratio. For the second scan with the other bipolar gradient, one obtains:

$$s_2(k_x,k_y) = \iint_{x,y} m_2(x,y) e^{-i[2\pi(k_x x + k_y y) - \gamma M_z v_z(x,y)]} dx dy \quad (2)$$

The phase difference images are reconstructed using the following Equation (3):

$$z_1 = m_1 e^{i\gamma M_z v_z}$$

$$z_2 = m_2 e^{-i\gamma M_z v_z}$$

$$\Delta\phi = \text{angle}(z_1 \times z_2^*) = 2\gamma M_z v_z \quad (3)$$

The phase difference method is commonly used to quantitatively assess the blood volume/velocity through a vessel of interest. An alternative method for processing the PC image data is complex difference (CD) processing, for example, as described in Dumoulin et al., "Three-dimensional phase contrast angiography", Magn Reson Med 1989; 9(1):139-149. In this technique, a CD image is calculated using:

$$CD = z_1 - z_2 = m_1 e^{i\gamma M_z v_z} - m_2 e^{-i\gamma M_z v_z} = m_1(e^{i\gamma M_z v_z} - e^{-i\gamma M_z v_z}) \quad (4)$$

where $m_1$ is assumed to be identical to $m_2$. The data value or signal in the CD image depends on the blood flow in a voxel of the image data. For stationary voxels, the signal difference between the two acquisitions is almost zero. Therefore, the CD image contains a data value or signal only in locations where there is blood flow resulting in a very sparse image. The present invention utilizes the sparsity of the CD image in implementing the inventive image reconstruction method 70.

For PC MR image processing in the prior art, CS reconstruction is performed simply by solving a pair of unconstrained optimization problems for each individual bipolar encoding image $m_i$:

$$\arg_{z_1} \min \|F_\Omega z_1 - s_1\|_2 + \lambda \|\Psi z_1\|_1$$

$$\arg_{z_2} \min \|F_\Omega z_2 - s_2\|_2 + \lambda \|\Psi z_2\|_1 \quad (5)$$

where $F_\Omega$ is the Fourier transform with under-sampling, $\Psi$ is a sparsifying transform, $s_i$ is the measurement for each of the two bipolar encodings with i=1 or 2, $z_i$ is the respective complex image, and $\lambda$ is the weight of the sparsity terms.

In the apparatus 40 and method 70 of the present invention, an additional constraint, not utilized in the prior art, is exploited for reconstructing phase contrast MR images in which the complex difference image is used as an additional constraint. The Lagrangian-form problems shown in Equation (5) are modified in the present invention to include this additional constraint term, such that:

$$\arg_{z_1} \min \|F_\Omega z_1 - s_1\|_2 + \lambda \|\Psi z_1\|_1 + \lambda_{CD} \|z_1 - z_2\|_1$$

$$\arg_{z_2} \min \|F_\Omega z_2 - s_2\|_2 + \lambda \|\Psi z_2\|_1 + \lambda_{CD} \|z_1 - z_2\|_1 \quad (6)$$

where is $|z_1 - z_2|$ is the complex difference (CD) image, and $\lambda$ and $\lambda_{CD}$ are the regularization parameters for balancing between data fidelity and image sparsity.

As described herein, in the prior art, the method described by King solves only one equation using a traditional conjugate gradient approach, as opposed to iteratively solving two equations in an alternating fashion as described in connection with Equation 6. Once the individual flow encoded images $m_1$, $m_2$, $m_3$, and $m_4$ are resolved, the present invention may be used either to generate flow images and/or to calculate a squareroot of sum of squares and then to create a MR angiogram, for example, using maximum intensity projection.

The present invention involves two steps. Initially, the inventive reconstruction method quantifies a fluid flow, such as a blood flow in a subject, for different acceleration rates using retrospectively under-sampled data from a fully-sampled acquisition. During experimental use of the apparatus 40 and method 70 of the present invention, an optimum set of reconstruction parameters were determined, which were used in the subsequent step with a prospectively under-sampled image acquisition, where the accuracy of the accelerated acquisition was determined.

During experimental use of the apparatus 40 and method 70 of the present invention, phase contrast images were acquired from the image data source 60 using an axial slice of the ascending aorta of subjects at the level of the bifurcation of the pulmonary artery. For the retrospective under-sampling in step 72, a prospectively ECG-triggered flow-encoded 2D PC cine MRI pulse gradient-echo imaging sequence was used with typical parameters of, for example: a field of view value FOV=320×400 mm$^2$, a resolution=2.5×2.5 mm$^2$, an acquisition matrix=128×160, a slice thickness=8 mm, TR/TE=4.6/2.7 ms, a flip angle=12°, a temporal resolution=28.3~39.1 ms, and a velocity-encoded value VENC=300 cm/s. In the experimental use of the present invention, the fully-sampled k-space data were acquired in fifteen healthy adult subjects (five males, age range: 20-70 years). The data were retrospectively under-sampled for various acceleration rates (R=2, 3, 4, and 5) by randomly discarding the outer k-space lines while keeping the center of k-space, to perform step 72. The size of the central k-space was set to be half of the size of the total number of k-space lines acquired at that acceleration rate. To allow a sufficient number of k-space lines around the center, the size of the center of k-space for different acceleration rates was not fixed.

Subsequently, accelerated PC MRI data was acquired in eleven subjects (four males, age range: 20-45 years) with the same imaging parameters as described above. To enable accelerated data acquisition with a random under-sampling pattern, the imaging pulse sequence was modified such that a fully-sampled central k-space was acquired, with 40, 26, 20, 16, and 14 $k_y$ lines out of total 160 $k_y$ lines for acceleration rates of 2, 3, 4, 5, and 6 respectively, and the remaining edges of the k-space were sampled randomly until a sufficient number of lines were acquired for a given acceleration rate. A modified low-to-high profile ordering was used to minimize artifacts due to rapid gradient switching, as described in Basha et al., "Minimization of Imaging Artifacts from Profile Ordering of Randomly Selected ky-kz Lines for Prospective Compressed-Sensing Acquisition in 3D Segmented SSFP and GRE Imaging", Proceedings of the 19th Annual Meeting of ISMRM. Volume 19. Montreal, Canada; 2011. p 1264; and Akcakaya et al., "Accelerated contrast-enhanced whole-heart coronary MRI using low-dimensional-structure self-learning and thresholding", Magn Reson Med 2012; 67(5):1434-1443.

Each subject was imaged with acceleration rates (R) of one (i.e. fully-sampled) to six. To assess the inter-scan variability, each scan was repeated twice, one after the other. In summary, each subject was imaged twelve times using six acceleration rates (R1 to R6) with one repeat scan for each acceleration rate.

Figure 4:
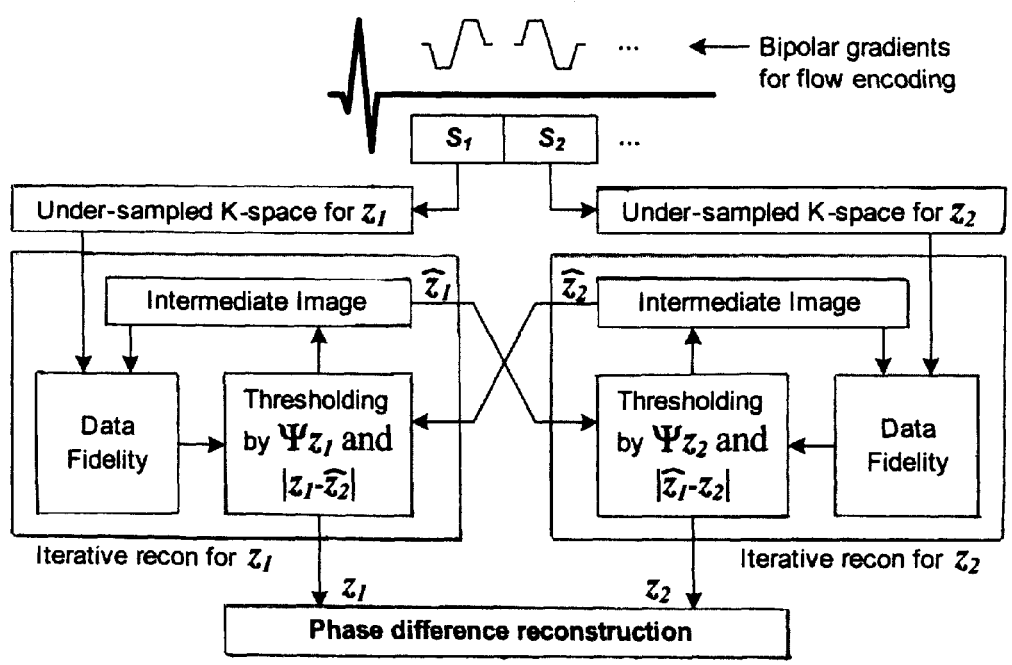
FIG. 4 is another flowchart illustrating iterative steps of the method in accordance with the exemplary embodiment of the present invention.
Figure 5:
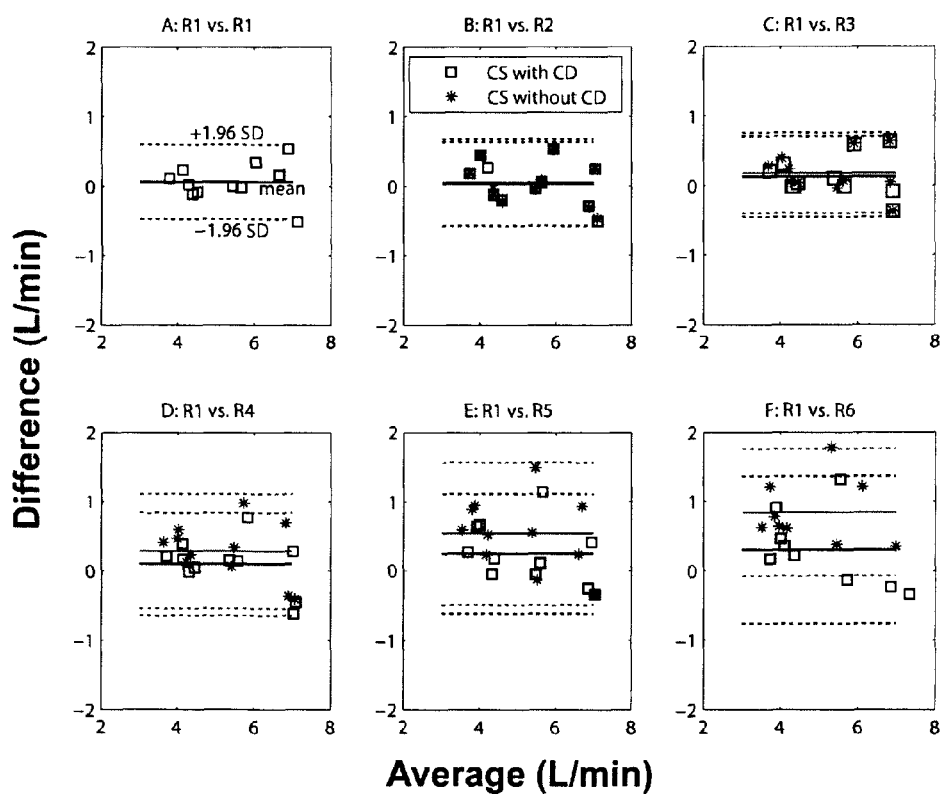
FIGS. 5A-5F illustrate a Bland-Altman analysis of the cardiac output using the present invention.
Figure 6:
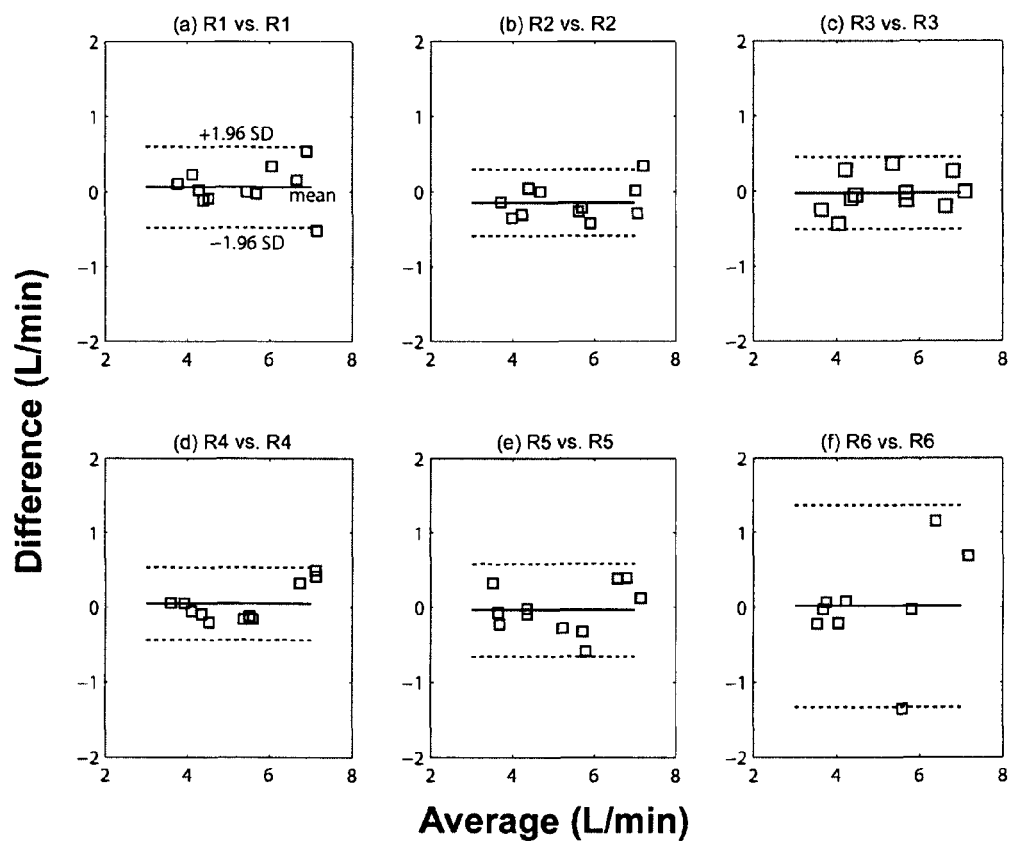
FIGS. 6A-6F depict a Bland-Altman analysis of the inter-scan reproducibility of a CS reconstruction with the CD constraint using the present invention.

The image reconstruction was performed according to the method 70 presented in FIGS. 3-4, which illustrates how the CS reconstruction procedure, applied in the present invention, utilizes the sparsity of the CD image and alternating minimization. Initially, the image data S1 and S2 from bipolar gradients for flow encoding are received from the image data source 60, and under-sampled image data for the images $z_1$ and $z_2$ are obtained as described herein. A data fidelity procedure, known in the art, is initially performed on the under-sampled image data.

Then, in step 74, initial estimates $\hat{z}_1$ and $\hat{z}_2$ of intermediate images are both set to all-zero images. Then, at each iteration, the method 70 keeps $\hat{z}_2$ fixed, and solves the first line of Equation (6) for an estimate $\hat{z}_1$ by performing the data fidelity procedure in step 76 and the thresholding procedure in step 78 using both the first sparsity term $\|\Psi z_1\|_1$ and the additional sparsity of the CD image $|z_1 - \hat{z}_2|$. Then $\hat{z}_1$ is kept fixed, and the second line of Equation (6) is solved for $\hat{z}_2$ using both $\|\Psi z_2\|_1$ and the sparsity of the CD image $|\hat{z}_1 - z_2|$ similarly. Such simultaneous calculations of the images $z_1$ and $z_2$ are shown in FIG. 4.

As shown in FIG. 4, iterative CS reconstruction of the phase contrast MR images using sparsity of the complex difference image is performed. The reconstruction consists of two separate iterative processes, each with two steps of data fidelity and thresholding. The thresholding step utilizes both the sparsifying transform of the image $\Psi z_i$ and the intermediate image of the other process for calculating the complex difference image. The unaliased phase difference image, as the reconstructed image, is then obtained using final estimation of the images $z_1$ and $z_2$.

Referring to FIGS. 3-4, the steps 76-78 are repeated until convergence, defined herein to be when the relative change of the norm of both images $z_1$ and $z_2$ becomes less than a predetermined threshold of, for example, $5\times10^{-4}$. In the present invention, Total Variation (TV) regularization was performed as the sparsifying transform $\Psi$, since TV has been shown in the prior art to be a good constraint for noise removal in image restoration, as described in Rudin et al., "Nonlinear total variation based noise removal algorithms", Physica D: Nonlinear Phenomena 1992; 60(1-4):259-268.

TV has been widely used in many CS MR studies, as described in Lustig et al., "The application of compressed sensing for rapid MR imaging", Magn Reson Med 2007; 58(6):1182-1195; and Block et al., "Undersampled radial MRI with multiple coils. Iterative image reconstruction using a total variation constraint", Magn Reson Med 2007; 57(6): 1086-1098.

The reconstruction of each image in step 84 is performed coil by coil for images from an MRI device with magnetic coils, using the fast alternating direction method for TVL1-L2 minimization, as described in Junfeng et al., "A fast alternating direction method for TVL1-L2 signal reconstruction from partial Fourier data", Selected Topics in Signal Processing, IEEE Journal of 2010; 4(2):288-297.

Using these two complex images $z_1$ and $z_2$, the apparatus 40 and method 70 of the present invention extract the flow information from the phase difference reconstruction of images of the subjects. The reconstruction procedure 70 described above can be considered as an alternating minimization formulation to solve the optimization problem involving the sum of the two objective functions. As described in Wang et al., "A New Alternating Minimization Algorithm for Total Variation Image Reconstruction", SIAM Journal on Imaging Sciences 2008; 1(3):248-272", the minimization of the sum of the two functions can be solved alternatively as follows, expressed in pseudo-code:

---

Let $J(z_1, z_2) = \|F_\Omega z_1 - s_1\|_2 + \|F_\Omega z_2 - s_2\|_2 + \lambda\|\Psi z_1\|_1 + \lambda\|\Psi z_2\|_1 + \lambda_{CD}\|z_1 - z_2\|_1$, $z_2 = 0$, and $k = 0$;
  While "not converged" Do
    Step 1: Fix $z_2 = z_2^k$ and minimize $J(z_1, z_2^k)$ in terms of $z_1$ and let $z_1^k = z_1$;

-continued

Step 2: Fix $z_1 = z_1^k$ and minimize $J(z_1^k, z_2)$ in terms of $z_2$ and let $z_2^{k+1} = z_2$;
Step 3: k = k + 1;
End Do.

The apparatus 40 and method 70 of the present invention, implementing the inventive reconstruction method with CS, are applied separately for all cardiac phases, which adds computational complexity to the image reconstruction. However, in processing images where there is minimal blood flow, the CD image in cardiac phases does not contain any or sufficient information except velocity noise resulting from the dominant phase error, and the image also does not add any or significant additional information to improve the reconstruction.

In addition, for each image reconstruction, the present invention may receive a user selection, through the input device 48, of a region of interest (ROI) manually drawn on corresponding magnitude images of the ascending aorta of a subject. For example, a doctor may select the ROI using a GUI implemented by the input device 48 and the output device 50, such as by moving a mouse on a display screen and/or moving a finger or stylus on a touch screen of the GUI, to delimit the ROI of the image data to be processed, so that the ROI may be manually corrected through the cardiac cycle for cardiac motion.

During experimental use of the apparatus 40 and method 70 of the present invention, the mean velocity of blood flow in each cardiac cycle and the cardiac output were calculated for each reconstruction of images. Bland-Altman analysis and Pearson correlation calculations were performed to compare the cardiac outputs, in liters per minute, reconstructed by CS reconstruction with and without using the CD image as a constraint. The cardiac output calculated by the reconstruction using the fully-sampled data was used as a reference.

Table 1 shows Bland-Altman analysis of the cardiac output for different under-sampling rates, in particular between the fully-sampled data and CS reconstruction of the retrospectively under-sampled data and relevant Pearson coefficients, r, for experimental use of the apparatus 40 and method 70 of the present invention.

There is excellent agreement between the acceleration rate R=1 (fully-sampled data) and the acceleration rate R=2 (correlation coefficient: 0.999), as well as between a rate R=1 and a rate R=3 (correlation coefficient: 0.999). Although the Pearson correlation coefficient r decreases for higher acceleration rates, it is always above 0.97, indicating good agreement between the accelerated image reconstruction and the reference. The results of the experimental use of the present invention with the retrospectively under-sampled data suggest that 5-fold accelerated PC MR utilizing the apparatus 40 and method 70 of the present invention, with the sparsity of the CD image as an additional constraint, is a feasible technique for the assessment of cardiac output measured through the ascending aorta.

TABLE 1

| Acceleration Rate (R) | Mean of difference (liters/min) | Upper 95% (liters/min) | Lower 95% (liters/min) | Pearson Coefficients r |
|---|---|---|---|---|
| 2 | −0.004 | 0.120 | −0.129 | 0.999 |
| 3 | 0.018 | 0.152 | −0.117 | 0.999 |
| 4 | 0.052 | 0.429 | −0.326 | 0.991 |
| 5 | 0.153 | 0.867 | −0.562 | 0.970 |

FIGS. 5A-5F illustrate the Bland-Altman analysis of the cardiac output of the prospectively accelerated acquisitions, and Table 2 illustrates a Bland-Altman analysis of the cardiac output between the fully-sampled data and two different CS reconstructions with and without use of CD image constraint for the prospectively under-sampled data. Table 2 summarizes the relevant mean and standard deviations of the differences between the fully-sampled data and CS reconstruction of the accelerated scan with and without use of the CD image constraint, for different rates, with R1 representing an acceleration rate R=1, R2 representing an acceleration rate R=2, etc.

The Bland-Altman analysis of the blood volume through the ascending aorta for scan/rescan variability is shown in FIG. 5A for the fully-sampled acquisitions (R1 vs. R1), and is shown in FIGS. 5B-5F illustrating the comparison between the fully-sampled data and reconstructions of prospectively accelerated scan with rates R equal to two through six using: CS with CD sparsity illustrates by a black square, and CS without CD sparsity illustrated by a black star. At lower acceleration rates R, for example, less than or equal to three, both reconstruction techniques yield clinically equivalent results. However, at high acceleration rates, CS reconstruction with CD sparsity results in superior flow measurements and smaller differences than the CS reconstruction without CD sparsity, when compared to the fully-sampled acquisition.

TABLE 2

| Acceleration Rate (R) | Use of CD constraint | Mean of difference (liters/min) | SD of difference (liters/min) | Upper 95% (liters/min) | Lower 95% (liters/min) |
|---|---|---|---|---|---|
| R1 vs. R1 | N/A | 0.0623 | 0.273 | 0.598 | −0.474 |
| R1 vs. R2 | with CD | 0.0530 | 0.319 | 0.678 | −0.572 |
|  | without CD | 0.0286 | 0.309 | 0.633 | −0.576 |
| R1 vs. R3 | with CD | 0.128 | 0.295 | 0.706 | −0.449 |
|  | without CD | 0.182 | 0.295 | 0.761 | −0.396 |
| R1 vs. R4 | with CD | 0.0930 | 0.378 | 0.833 | −0.647 |
|  | without CD | 0.280 | 0.421 | 1.11 | −0.545 |
| R1 vs. R5 | with CD | 0.246 | 0.441 | 1.11 | −0.618 |
|  | without CD | 0.536 | 0.526 | 1.57 | −0.496 |
| R1 vs. R6 | with CD | 0.299 | 0.542 | 1.36 | −0.763 |
|  | without CD | 0.841 | 0.470 | 1.76 | −0.0790 |

FIG. 5A shows the inter-scan reproducibility of the fully-sampled data, which shows differences between two separate scans under the same scan conditions. FIGS. 5B-5F show agreement between a fully-sampled acquisition and the accelerated acquisitions for rates R equal to two through six. FIGS. 5A-5F also compare two different CS image processing methods, one utilizing CD sparsity and another one that does not. Black squares and black solid lines indicate that the variation of the difference between a fully-sampled scan and an accelerated scan reconstructed with the method 70 of the present invention is in the range of that of the scan-rescan of the fully-sampled data for up to acceleration rate of four. The variation is also in the acceptable range with rate of five. However, there is a larger variation (by 98% compared to the reproducibility of the fully-sampled data) in the flow measurement for rate of six as seen in Table 2. Furthermore, larger standard deviations are observed in the difference between the fully-sampled scan and accelerated scan reconstructed without the CD constraint, especially for high acceleration rates (12% and 19% increase for rates four and five, respectively, compared to the reconstruction with CD constraint) as depicted in Table 2. These differences are more positively biased for the case of the CS without CD constraint, which would lead to a greater underestimation of the velocity of the blood.

FIGS. 6A-6F illustrate Bland-Altman analysis of the blood volume through the ascending aorta with different scan/rescan variability, demonstrating the inter-scan reproducibility of the CS reconstruction with the CD constraint. FIG. 6A shows the inter-scan reproducibility of the fully-sampled data acquisitions (R1 vs. R1), and FIGS. 6B-6F show the inter-scan reproducibility of the prospectively accelerated acquisitions for rates R equal to two through six, respectively, using CS reconstructions with CD sparsity. Up to acceleration rate of five, the ranges of the standard deviations are not greater than the standard deviation of the reference in FIG. 6A. The standard deviation of the data in FIG. 6F is comparatively higher than the standard deviation of the data in FIG. 6A. Accordingly, the reconstruction technique of the apparatus 40 and method 70 of the present invention yields clinically equivalent results with the fully-sampled acquisitions.

Figure 7:
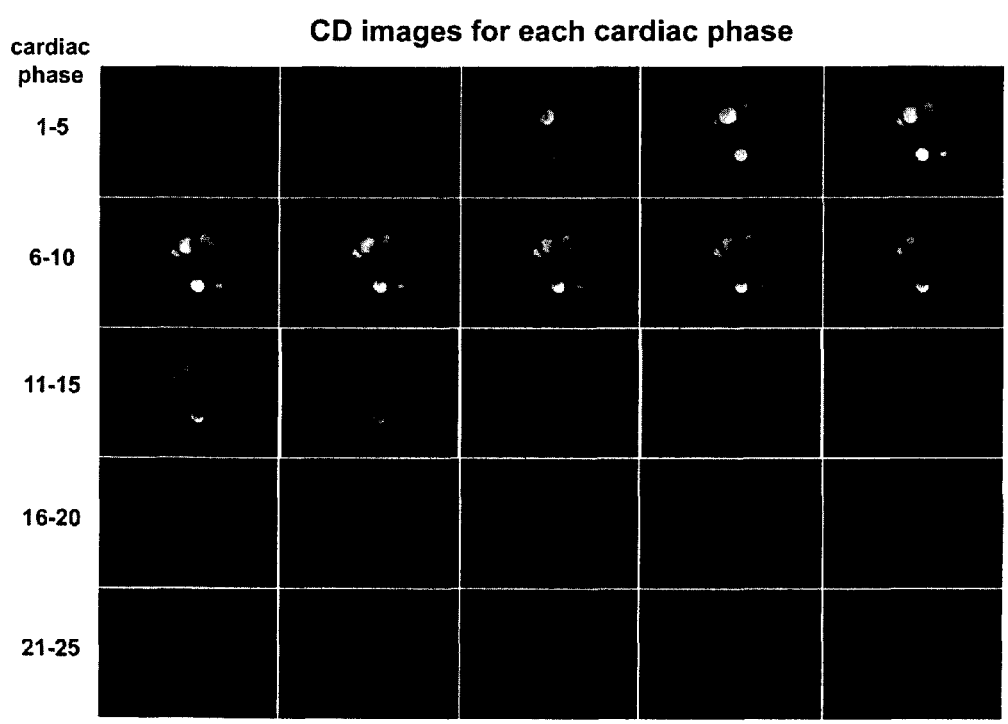
FIG. 7 illustrates the CD images for all 25 cardiac phases of a healthy subject using the present invention.
Figure 8:
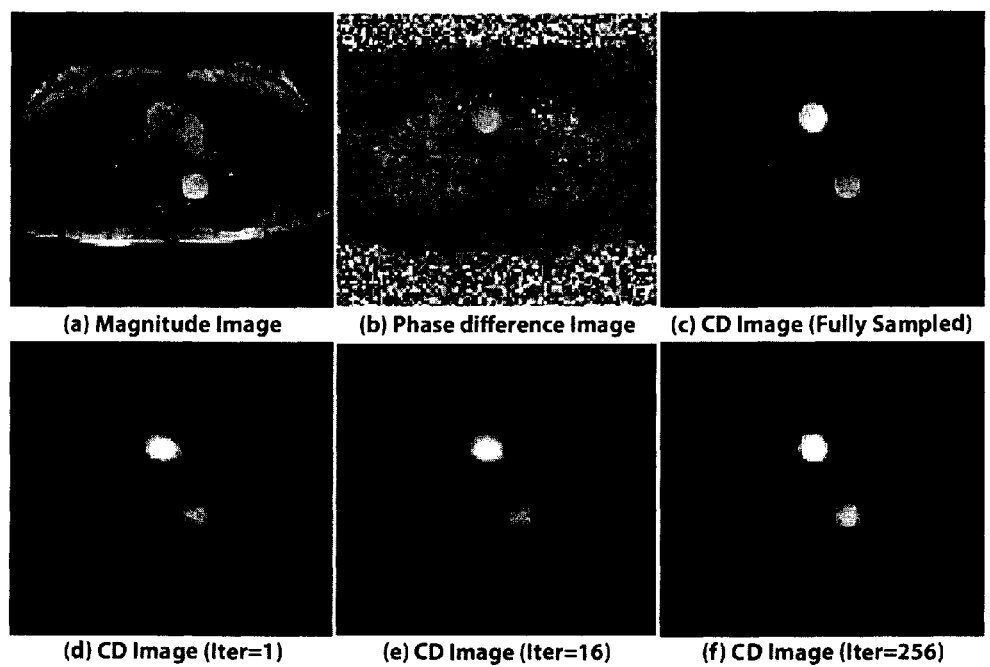
FIGS. 8A-8F show the convergence speed of the reconstruction of images using the present invention.

FIG. 7 shows the magnitude CD images for all 25 cardiac phases of a healthy subject. In the CD images of the first 10 phases, vessels are clearly seen for the ascending and descending aortas. Therefore, CD images are used as an additional constraint for the CS method of the present invention for these phases. However, CD images of the latter 15 phases do not have much information about the vessels compared to the background image. Therefore there might be a chance that the thresholding operations exclude some important signals for those phases. In these cases, it is beneficial not to use the CD images for CS reconstruction in order to improve the performance and also to reduce the complexity. Therefore, the additional CD constraint was only used during the time when the aortic flow was high enough for the CD image to have substantial vessel signal or data for measurement and reconstruction. The cardiac phases that use the CD constraint for the reconstruction are set as the first 40% of the whole cardiac cycle. For the first 40% of the cardiac cycle that uses the CD constraint, the values of parameters $\lambda$ and $\lambda_{CD}$ were set to equal $10^{-4}$. For the latter 60% of the cardiac cycle, the parameters are set such that $\lambda_{CD}=0$ and $\lambda=10^{-4}$ to implement the regular CS method as shown in the Equation (5). For comparison, images were also reconstructed without the use of the CD constraint throughout the cardiac cycle, as given in Equation (5).

FIGS. 8A-8F shows the convergence speed of the reconstruction method used in the apparatus 40 and method 70 of the present invention. Sample phase contrast images from a healthy subject are shown in FIGS. 8A-8C which are fully-sampled images of an axial slice of the ascending aorta at the level of the bifurcation of the pulmonary artery. A magnitude image is shown in FIG. 8A, a phase difference image is shown in FIG. 8B, and a complex difference image reconstructed using fully-sampled k-space data is shown in FIG. 8C.

The corresponding CD images in FIGS. 8D-8F for different iterations (iterations of 1, 16, and 256, respectively) of the reconstruction method, used in the apparatus 40 and method 70 of the present invention, are applied to a retrospectively under-sampled k-space dataset of the same subject with an acceleration rate of five. Aliasing artifacts and blurring are clearly visible in the CD image at the start of the method seen in FIG. 8D. However, through the iterative CS reconstruction method 70 of the present invention, the vessel walls appear sharper, and the CD image becomes sparser and gets close to being substantially identical to the CD image of the fully-sampled data in FIG. 8F.

The apparatus 40 and method 70 of the present invention implement the newly-developed CS reconstruction method, disclosed herein, for accelerated phase contrast CMR. The sparsity of the CD image was included as an additional constraint for the minimization problem in this approach. In experimental tests of the present invention, no systematic variation was observed for the cardiac output measurements between the fully-sampled reference data and those reconstructed with the disclosed image reconstruction apparatus 40 and method 70 of the present invention up to acceleration rate of five.

In previous studies on the utility of CS in accelerated PC MR in the prior art, underestimation of the velocities of voxels of interest was noted as an issue. Underestimation can be seen as the bias of the Bland-Altman analysis comparing fully-sampled PC acquisition and reconstructions of the accelerated PC acquisitions. However, in experimental implementation of the apparatus 40 and method 70 of the present invention, the CS reconstruction which uses total variation of the image without CD sparsity suffered from the underestimation of the cardiac output as seen by the positive bias of the difference. However, by utilizing the CD image and an additional sparsifying constraint, the bias of the difference of the cardiac output was significantly reduced for acceleration rates of up to five.

One of the major issues for CS might be the spatial resolution loss or blurring of the reconstructed image. Over the past years, there have been various improved reconstruction methods that address this issue for high-resolution cardiac MRI, as described in Akcakaya et al., "Accelerated contrast-enhanced whole-heart coronary MRI using low-dimensional-structure self-learning and thresholding", Magn Reson Med 2012; 67(5):1434-1443; Akcakaya et al., "Low-dimensional-structure self-learning and thresholding: regularization beyond compressed sensing for MRI reconstruction", Magn Reson Med 2011; 66(3):756-767; and Akcakaya et al., "Accelerated Late Gadolinium Enhancement Cardiac MRI with Isotropic Spatial Resolution Using Compressed Sensing: Initial Experience", Radiology in press.

However, for PC imaging, the issue of blurring has less impact on quantification of the flow. First, the spatial resolution is much lower than needed for the assessment of coronary lesions or scars. Second, during the analysis, pixels in the vessel wall are intentionally avoided to reduce the partial volume errors. Third, quantification of flow is usually performed over the entire cardiac cycle using average blood flow velocity.

The per-iteration computational cost of the disclosed apparatus 40 and method 70 of the present invention is four FFTs (including two inverse FFTs) and four thresholding operations, all applied to images of the size of the 2D phase image. The reconstruction time is dependent on the actual number of cardiac phases and the required number of iterations, but the reconstruction time is approximately less than 20 minutes using the predetermined software 46, developed using "MATLAB", with the image processing system 40 implemented, for example, on a 64-bit personal computer running on the "WINDOWS" operating system, commercially available from "MICROSOFT CORP.", with a dual core CPU and 8 GB of RAM. The reconstruction time may be further reduced to a clinically acceptable range through the use of parallel programming and a graphics processing unit, as described in Nam et al., "Compressed sensing reconstruction for whole-heart imaging with 3D radial trajectories: A graphics processing unit implementation", Magn Reson Med in press.

In the preferred embodiment of the apparatus 40 and method 70 of the present invention, the best mode of operation provides a maximum acceleration rate of five. In alternative embodiments, higher acceleration rates greater than or equal to six may be possible with a larger number of coil elements in the MRI system of FIG. 1 as the image data source 60, since images will be better localized in different coils. In additional alternative embodiments of the present invention, an optimal combination of the disclosed apparatus 40 and method 70 with parallel imaging techniques may also be possible.

In conclusion, the disclosed apparatus 40 and method 70 of the present invention have been developed and evaluated to provide an improved reconstruction technique for accelerated PC CMR that utilizes the sparsity of the CD of the two flow-encoded images. Accordingly, using the present invention, accelerated phase contrast cine MRI using compressed sensing (CS) with additional constraints using image-domain sparsity of the complex difference of images allows for accurate measurements of the blood flow in, for example, the aorta of a patient.

The above-described apparatus and methods according to the present invention can be implemented in hardware, firmware or as software or computer code that can be stored in a recording medium such as a CD ROM, a RAM, a ROM, a floppy disk, DVDs, a hard disk, a magnetic storage media, an optical recording media, or a magneto-optical disk or computer code downloaded over a network originally stored on a remote recording medium, a computer readable recording medium, or a non-transitory machine readable medium and to be stored on a local recording medium, so that the methods described herein can be rendered in such software that is stored on the recording medium using a general purpose computer, a digital computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein.

What is claimed is:

1. An apparatus for processing image data, the apparatus comprising:
a processor, operating predetermined software, for receiving the image data of a subject from a data source, and for applying a compressed sensing (CS) reconstruction method utilizing a sparsifying transform with a complex difference of the image data being a constraint for imaging of at least one of blood flow and magnetic resonance angiography to generate a reconstructed image of the at least one of blood flow and magnetic resonance angiography from the image data; and
an output device for outputting the reconstructed image.

2. The apparatus of claim 1, wherein the image data corresponds to at least one of angiographic data, four dimensional blood flow data, neurological blood flow data, abdominal blood flow data, and peripheral blood flow data in the subject.

3. The apparatus of claim 1, further comprising:
a magnetic resonance image (MRI) system for obtaining the image data of the subject.

4. An apparatus for processing image data, the apparatus comprising:
a processor, operating predetermined software, for receiving the image data from a data source, and for applying a compressed sensing (CS) reconstruction method to the image data, which uses a sparsifying transform with a complex difference of the image data being a constraint to generate a reconstructed image from the image data; and
an output device for outputting the reconstructed image.

5. The apparatus of claim 4, wherein the CS reconstruction method uses regularization parameters when processing the complex difference images derived from the image data for balancing between data fidelity and image sparsity.

6. The apparatus of claim 4, wherein the image data is under-sampled from a fully-sampled k-space of the image data.

7. The apparatus of claim 4, wherein the data source is a magnetic resonance imaging (MRI) device having a plurality of coils for generating the image data from a living subject.

8. The apparatus of claim 4, wherein the CS reconstruction method iteratively updates estimates of phase images of the image data.

9. The apparatus of claim 8, wherein the iterative updating continues until a convergence occurs when a relative change of the norm of the phase images becomes less than a predetermined convergence threshold.

10. The apparatus of claim 8, wherein the iterative updating includes performing a thresholding procedure using a sparsity of complex difference images.

11. An apparatus for processing magnetic resonance image (MRI) data, the apparatus comprising:
an input device for receiving the MRI data of a fluid flow in a living subject from an MRI device having a plurality of coils, and for generating selected image data from received inputs;
a processor, operating predetermined software, for receiving the selected image data, and for applying a compressed sensing (CS) reconstruction method to the image data utilizing a sparsifying transform with a complex difference of the image data being a constraint to generate a reconstructed image from the image data; and
an output device for outputting the reconstructed image of the fluid flow in the living subject.

12. The apparatus of claim 11, wherein the CS reconstruction method uses regularization parameters when processing complex difference images derived from the image data for balancing between data fidelity and image sparsity.

13. The apparatus of claim 11, wherein the image data is under-sampled from a fully-sampled k-space of the image data.

14. The apparatus of claim 11, wherein the CS reconstruction method iteratively updates estimates of phase images of the image data.

15. The apparatus of claim 14, wherein the iterative updating continues until a convergence occurs when a relative change of the norm of the phase images becomes less than a predetermined convergence threshold.

16. The apparatus of claim 14, wherein the iterative updating includes performing a thresholding procedure using sparsity of complex difference images.

17. A method for processing image data, the method comprising:
receiving the image data of a subject at a processor, operating predetermined software, from a data source;
applying a compressed sensing (CS) reconstruction method to the image data, including applying a sparsifying transform using with a complex difference of the image data being a constraint of the reconstruction;
generating a reconstructed image from the image data; and
outputting the reconstructed image.

18. The method of claim 17, wherein the image data corresponds to at least one of angiographic data, four dimensional blood flow data, neurological blood flow data, abdominal blood flow data, and peripheral blood flow data in the subject.

19. The method of claim 17, further comprising:
generating the image data by under-sampling from a fully-sampled k-space of the image data.

20. The method of claim 17, wherein the data source is a magnetic resonance imaging (MRI) device having a plurality of coils for generating the image data from a living subject.

21. The method of claim 17, wherein applying the CS reconstruction method includes:
iteratively updating estimates of phase images of the image data.

22. An apparatus for processing image data, the apparatus comprising:
a processor, operating predetermined software, for receiving the image data from a data source, wherein the image data corresponds to angiographic data, and for applying a compressed sensing (CS) reconstruction method utilizing a complex difference of the image data as a sparsifying transform with a complex difference or the image data being a constraint for imaging of at least one of blood flow and magnetic resonance angiography to generate a reconstructed image of the at least one of blood flow and magnetic resonance angiography from the image data; and
an output device for outputting the reconstructed image.

23. The apparatus of claim 22, further comprising:
a magnetic resonance image (MRI) system for obtaining the image data of a subject.

24. An apparatus for processing image data, the apparatus comprising:
a processor, operating predetermined software, for receiving the image data from a data source, wherein the image data corresponds to four-dimensional blood flow, and for applying a compressed sensing (CS) reconstruction method utilizing a complex difference of the image data as a sparsifying transform with a complex difference of the image data being a constraint for imaging of at least one of blood flow and magnetic resonance angiography to generate a reconstructed image of the at least one of blood flow and magnetic resonance angiography from the image data; and
an output device for outputting the reconstructed image.

25. The apparatus of claim 24, further comprising:
a magnetic resonance image (MRI) system for obtaining the image data of a subject.

26. The apparatus of claim 1, wherein a sparsity transformation comprises:

$$\arg_{z_1}\min\|F_\Omega z_1 - s_1\|_2 + \lambda\|\Psi z_1\|_1 + \lambda_{CD}\|z_1 - z_2\|_1$$
$$\arg_{z_2}\min\|F_\Omega z_2 - s_2\|_2 + \lambda\|\Psi z_2\|_1 + \lambda_{CD}\|z_1 - z_2\|_1 \quad (6)$$

where $F_\Omega$ is a Fourier transform with under-sampling, $\Psi$ is a sparsifying transform, $s_i$ is a measurement for each of two bipolar encodings with i=1 or 2, $z_i$ is the respective complex image, where is $|z_1 - z_2|$ is the complex difference (CD) image, and $\lambda$ and $\lambda_{CD}$ are regularization parameters for balancing between data fidelity and image sparsity.

27. The apparatus of claim 4, wherein a sparsity transformation comprises:

$$\arg_{z_1}\min\|F_\Omega z_1 - s_1\|_2 + \lambda\|\Psi z_1\|_1 + \lambda_{CD}\|z_1 - z_2\|_1$$
$$\arg_{z_2}\min\|F_\Omega z_2 - s_2\|_2 + \lambda\|\Psi z_2\|_1 + \lambda_{CD}\|z_1 - z_2\|_1 \quad (6)$$

where $F_\Omega$ is a Fourier transform with under-sampling, $\Psi$ is a sparsifying transform, $s_i$ is a measurement for each of two bipolar encodings with i=1 or 2, $z_i$ is the respective complex image, where is $|z_1 - z_2|$ is the complex difference (CD) image, and $\lambda$ and $\lambda_{CD}$ are regularization parameters for balancing between data fidelity and image sparsity.

28. The apparatus of claim 11, wherein a sparsity transformation comprises:

$$\arg_{z_1}\min\|F_\Omega z_1 - s_1\|_2 + \lambda\|\Psi z_1\|_1 + \lambda_{CD}\|z_1 - z_2\|_1$$
$$\arg_{z_2}\min\|F_\Omega z_2 - s_2\|_2 + \lambda\|\Psi z_2\|_1 + \lambda_{CD}\|z_1 - z_2\|_1 \quad (6)$$

where $F_\Omega$ is a Fourier transform with under-sampling, $\Psi$ is a sparsifying transform, $s_i$ is a measurement for each of two bipolar encodings with i=1 or 2, $z_i$ is the respective complex image, where is $|z_1 - z_2|$ is the complex difference (CD) image, and $\lambda$ and $\lambda_{CD}$ are regularization parameters for balancing between data fidelity and image sparsity.

29. The method of claim 17, wherein a sparsity transformation comprises:

$$\arg_{z_1}\min\|F_\Omega z_1 - s_1\|_2 + \lambda\|\Psi z_1\|_1 + \lambda_{CD}\|z_1 - z_2\|_1$$
$$\arg_{z_2}\min\|F_\Omega z_2 - s_2\|_2 + \lambda\|\Psi z_2\|_1 + \lambda_{CD}\|z_1 - z_2\|_1 \quad (6)$$

where $F_\Omega$ is a Fourier transform with under-sampling, $\Psi$ is a sparsifying transform, $s_i$ is a measurement for each of two bipolar encodings with i=1 or 2, $z_i$ is the respective complex image, where is $|z_1 - z_2|$ is the complex difference (CD) image, and $\lambda$ and $\lambda_{CD}$ are regularization parameters for balancing between data fidelity and image sparsity.

30. The apparatus of claim 22, wherein a sparsity transformation comprises:

$$\arg_{z_1}\min\|F_\Omega z_1 - s_1\|_2 + \lambda\|\Psi z_1\|_1 + \lambda_{CD}\|z_1 - z_2\|_1$$
$$\arg_{z_2}\min\|F_\Omega z_2 - s_2\|_2 + \lambda\|\Psi z_2\|_1 + \lambda_{CD}\|z_1 - z_2\|_1 \quad (6)$$

where $F_\Omega$ is a Fourier transform with under-sampling, $\Psi$ is a sparsifying transform, $s_i$ is a measurement for each of two bipolar encodings with i=1 or 2, $z_i$ is the respective complex image, where is $|z_1 - z_2|$ is the complex difference (CD) image, and $\lambda$ and $\lambda_{CD}$ are regularization parameters for balancing between data fidelity and image sparsity.

31. The apparatus of claim 24, wherein a sparsity transformation comprises:

$$\arg_{z_1}\min\|F_\Omega z_1 - s_1\|_2 + \lambda\|\Psi z_1\|_1 + \lambda_{CD}\|z_1 - z_2\|_1$$
$$\arg_{z_2}\min\|F_\Omega z_2 - s_2\|_2 + \lambda\|\Psi z_2\|_1 + \lambda_{CD}\|z_1 - z_2\|_1 \quad (6)$$

where $F_\Omega$ is a Fourier transform with under-sampling, $\Psi$ is a sparsifying transform, $s_i$ is a measurement for each of two bipolar encodings with i=1 or 2, $z_i$ is the respective complex image, where is $|z_1 - z_2|$ is the complex difference (CD) image, and $\lambda$ and $\lambda_{CD}$ are regularization parameters for balancing between data fidelity and image sparsity.

* * * * *

UNITED STATES PATENT AND TRADEMARK OFFICE
CERTIFICATE OF CORRECTION

PATENT NO.       : 9,081,074 B2  
APPLICATION NO.  : 13/590602  
DATED            : July 14, 2015  
INVENTOR(S)      : Yongjun Kwak et al.

Page 1 of 1

It is certified that error appears in the above-identified patent and that said Letters Patent is hereby corrected as shown below:

In the Specification

Column 1, Line 6 should read as follows:
--...This invention was made with government support under EB008743 and RR0257758 awarded by NIH. The government has certain rights in the invention...--

Signed and Sealed this
Tenth Day of November, 2015

Michelle K. Lee
*Director of the United States Patent and Trademark Office*